US009419300B2

(12) United States Patent
Hamrock et al.

(10) Patent No.: US 9,419,300 B2
(45) Date of Patent: Aug. 16, 2016

(54) PROTON CONDUCTING MATERIALS (75) Inventors: Steven Joseph Hamrock, Stillwater, MN (US); Mark Steven Schaberg, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 952 days.

(21) Appl. No.: 13/640,382

(22) PCT Filed: Mar. 23, 2011

(86) PCT No.: PCT/US2011/029555
§ 371 (c)(1),
(2), (4) Date: Oct. 10, 2012

(87) PCT Pub. No.: WO2011/129967
PCT Pub. Date: Oct. 20, 2011

(65) Prior Publication Data
US 2013/0029249 A1    Jan. 31, 2013

Related U.S. Application Data (60) Provisional application No. 61/325,062, filed on Apr. 16, 2010.

(51) Int. Cl.
*B01J 39/20*    (2006.01)
*C07C 303/02*    (2006.01)
(Continued)

(52) U.S. Cl.
CPC ........... *H01M 8/1039* (2013.01); *C07C 315/04* (2013.01); *C08F 8/12* (2013.01);
(Continued)

(58) Field of Classification Search
None
See application file for complete search history.

(56) References Cited

U.S. PATENT DOCUMENTS 2,732,398 A   1/1956   Brice
4,329,478 A   5/1982   Behr
(Continued)

FOREIGN PATENT DOCUMENTS

CN   1500075   5/2004
CN   101426836   5/2009
(Continued)

OTHER PUBLICATIONS

Alberti, et al., "Protonic conductivity of layered zirconium phosphonates containing—SO$_3$H groups. I. Preparation and characterization of a mixed zirconium phosphonate of composition Zr(O$_3$PR) $_{0.73}$ (O$_3$PR')$_{1.27}$ •$n$H$_2$O, with R'=-C$_6$H$_4$-SO$_3$H and R' =-CH$_2$-OH" *Solid State Ionics*, vol. 50, (1992), pp. 315-322.
(Continued)

*Primary Examiner* — Ula C Ruddock
*Assistant Examiner* — Matthew Van Oudenaren
(74) *Attorney, Agent, or Firm* — Julie Lapos-Kuchar; Stephen Crooks; Gregory D. Allen (57) ABSTRACT The description includes materials that may be useful for fuel cell applications such as in the manufacture of fuel cell electrodes, proton exchange membranes (PEM), as catalyst additives or in tie layers designed to be thermally and chemically robust while operating within a fuel cell's harsh environment at higher temperatures and to conduct protons, with significantly higher levels of bound acidic groups, while in a low hydration state. Methods of making the materials are also described.

17 Claims, 2 Drawing Sheets (51) Int. Cl.

| | | |
|---|---|---|
| *C07C 309/07* | (2006.01) | |
| *H01M 8/10* | (2016.01) | |
| *C07C 315/04* | (2006.01) | |
| *C08G 75/23* | (2006.01) | |
| *C08L 81/06* | (2006.01) | |
| *H01M 4/86* | (2006.01) | |
| *C08F 8/34* | (2006.01) | |
| *C08F 214/26* | (2006.01) | |
| *C08F 8/12* | (2006.01) | |
| *C08F 8/26* | (2006.01) | |
| *C08F 8/30* | (2006.01) | |

(52) U.S. Cl.
CPC .. *C08F 8/26* (2013.01); *C08F 8/30* (2013.01); *C08F 8/34* (2013.01); *C08F 214/26* (2013.01); *C08G 75/23* (2013.01); *C08L 81/06* (2013.01); *H01M 4/8668* (2013.01); *C08F 2810/50* (2013.01); *C08J 2381/06* (2013.01); *H01M 8/103* (2013.01); *H01M 8/1025* (2013.01); *H01M 8/1027* (2013.01); *H01M 8/1032* (2013.01); *H01M 8/1044* (2013.01); *H01M 2300/0082* (2013.01); *Y02E 60/521* (2013.01); *Y02P 70/56* (2015.11)

(56) References Cited

U.S. PATENT DOCUMENTS

| | | | |
|---|---|---|---|
| 4,343,749 A | 8/1982 | Siegemund | |
| 4,386,214 A | 5/1983 | Behr | |
| 4,423,197 A | 12/1983 | Behr | |
| 5,011,983 A * | 4/1991 | Behr | C07C 309/00 562/113 |
| 5,463,005 A | 10/1995 | Desmarteau | |
| 5,514,493 A | 5/1996 | Waddell | |
| 5,910,378 A | 6/1999 | Debe | |
| 6,090,895 A | 7/2000 | Mao | |
| 6,254,978 B1 | 7/2001 | Behr | |
| RE37,307 E | 8/2001 | Behr | |
| 6,277,512 B1 | 8/2001 | Hamrock | |
| RE37,656 E | 4/2002 | Bahar | |
| RE37,701 E | 5/2002 | Bahar | |
| 6,461,724 B1 | 10/2002 | Radovanovic | |
| 6,624,328 B1 | 9/2003 | Guerra | |
| 6,683,209 B2 | 1/2004 | Hamrock | |
| 6,727,386 B2 | 4/2004 | Hamrock | |
| 7,060,738 B2 | 6/2006 | Jing | |
| 7,060,756 B2 | 6/2006 | Jing | |
| 7,071,271 B2 | 7/2006 | Thaler | |
| 7,074,841 B2 | 7/2006 | Yandrasits | |
| 7,112,614 B2 | 9/2006 | Jing | |
| 7,173,067 B2 | 2/2007 | Guerra | |
| 7,259,208 B2 | 8/2007 | Guerra | |
| 7,326,737 B2 | 2/2008 | Guerra | |
| 7,338,692 B2 | 3/2008 | Smith . | |
| 7,348,088 B2 | 3/2008 | Hamrock | |
| 7,449,573 B2 | 11/2008 | Kodama | |
| 7,572,534 B2 | 8/2009 | Frey | |
| 2002/0002240 A1 | 1/2002 | Michot | |
| 2002/0160272 A1 | 10/2002 | Tanaka | |
| 2004/0116742 A1 | 6/2004 | Guerra | |
| 2004/0122256 A1 | 6/2004 | Ikeda | |
| 2005/0209421 A1 | 9/2005 | Hoshi | |
| 2007/0088142 A1 | 4/2007 | Ikeda | |
| 2007/0099052 A1 | 5/2007 | Frey | |
| 2007/0099053 A1 | 5/2007 | Frey | |
| 2009/0169959 A1 | 7/2009 | Pierpont | |
| 2009/0208809 A1 | 8/2009 | Hamrock | |
| 2009/0269644 A1 * | 10/2009 | Hamrock | C07F 9/3834 429/413 |
| 2010/0062314 A1 | 3/2010 | Frey | |
| 2010/0174042 A1 | 7/2010 | Yamakawa | |
| 2010/0233617 A1 | 9/2010 | Wada | |
| 2012/0156618 A1 | 6/2012 | Takahashi | |

FOREIGN PATENT DOCUMENTS

| | | |
|---|---|---|
| EP | 0047946 | 6/1983 |
| EP | 1736825 | 12/2006 |
| JP | 2005-275153 | 10/2005 |
| JP | 2007-95433 A | 4/2007 |
| JP | 2009-102490 | 5/2009 |
| JP | 2009-192617 | 8/2009 |
| JP | 2011-140605 | 7/2011 |
| WO | WO 99/07750 | 2/1999 |
| WO | WO 2004056726 | 7/2004 |
| WO | WO 2007/125919 | 11/2007 |
| WO | WO 2010/0150917 | 12/2010 |

OTHER PUBLICATIONS

Alberti, et al., "Protonic conductivity of layered zirconium phosphonates containing—SO₃H groups. III. Preparation and characterization of y-zirconium sulfoaryl phosphonates", *State Ionics*, vol. 84, (1996), pp. 97-104.

Arcella, et al,. "Hyflon Ion Membranes for Fuel Cells", *Industrial Engineering Chemistry Research*, (2005), vol. 44, No. 20, pp. 7646-7651.

Geiculescu, et al., "Dilithium bis[(perfluoroalkyl]diimide salts as electrolytes for rechargeable lithium batteris", *Journal of Fluorine Chemistry*, (2004), vol. 125, pp. 1179-1185.

Hickner, et al., "Alternative Polymer Systems for Protone Exchange Membranes (PEMs)", *Chemical Review*, (2004), vol. 104, No. 10, pp. 4587-4612.

Katsoulis, "A Survey of Applications of Polyoxometalates", *Chemical Reviews*, (1998), vol. 98, No. 1, pp. 359-387.

Kim, et al., "Synthesis, Structure, Spectroscopic Properties, and Hydrolytic Chemistry of Organophosphonoyl Polyoxotungstates of Formula $[C_6H_5P(O)]_2X^{n+}W_{11}O_{39}^{(8-n)-}(X^{n+}=P^{5+}, Si^{4+})$", *Inorganic Chemistry*, (1992), vol. 31, No. 25, pp. 5316-5324.

Mayer, et al. "Organophosphoryl derivatives of trivacant tungstophosphates of general formula $\alpha\text{-}A\text{-}[PW_9O_{34}(RPO)_2]^{5-}$: synthesis and structure determination by multinuclear magnetic resonance spectroscopy ($^{31}P$, $^{183}W$ )" *Chem. Soc., Dalton. Trans.* (1998), pp. 7-13.

Mayer, et al. "Organic—Inorganic Hybrids Based on Polyoxometalates. 5.¹Synthesis and Structural Characterization of Bis(organophosphoryl)decatungstosilicates [y-$SiW_{10}O_{36}$((RPO)₂⁴⁻", *Inorganic Chemistry*, (1999), vol. 38, pp. 6152-6158.

Mazeaud, et al., "Coordination Chemistry of Polyoxometalates: Rational Synthesis of the Mixed Organosilyl Derivatives of Trivacant Polyoxotungstates α-A-[PW₉O₃₄(tBuSiO)₃(RSi)]³⁻and α-B-[AsW₉O₃₃ (tBuSiO)₃(HSi)]⁵⁻***", *Angew. Chem., Int. Ed.Engl.* (1996), vol. 35, pp. 1961-1964.

Yang, et al., "The Preparation and Ion-Exchange Properties of Zirconium Sulphophosphoates", *Reactive Polymers*, vol. 5, (1987), pp. 13-21.

* cited by examiner

PROTON CONDUCTING MATERIALS

CROSS REFERENCE TO RELATED APPLICATION

This application is a national stage filing under 35 U.S.C. 371 of PCT/US2011/029555, filed on Mar. 23, 2011, which claims priority to U.S. Provisional Patent Application No. 61/325,062, filed Apr. 16, 2010, the disclosure of which is incorporated by reference herein in its entirety.

This invention was made with U.S. Government support under Cooperative Agreement DE-FG36-07GO17006 awarded by DOE. The U.S. Government has certain rights in this invention.

FIELD OF THE DISCLOSURE

This disclosure relates to materials that may be useful as ionomers or polymer ionomers.

BACKGROUND OF THE DISCLOSURE

Preparation and reactions of omega-halosulfonyl perfluoroalkanesulfonates are disclosed in U.S. Pat. No. 5,011,983 (Behr), the disclosure of which is incorporated herein by reference.

Reactions of cyclic perfluoroaliphaticdisulfonic acid anhydrides with amines to form sulfonamide derivatives are disclosed in U.S. Pat. No. 4,329,478 (Behr), U.S. Pat. No. 4,386,214 (Behr), and U.S. Pat. No. 4,423,197 (Behr), the disclosures of which are each incorporated herein by reference.

Perfluoroalkylsulfonates, sulfonimides and electrolytes containing them are disclosed in U.S. Pat. No. 5,514,493 (Waddell et al), the disclosure of which is incorporated herein by reference.

There is a need for improved ionomeric materials and methods of making the ionomeric materials.

SUMMARY

An embodiment of the current disclosure includes a method of making a compound according to formula I:

$$FSO_2(CF_2)_nSO_3Y \quad\quad (I)$$

where Y is chosen from the group consisting of H or a suitable countercation, and where n is 1-6, and the method comprises steps of:
(a) providing a compound according to formula II:

$$FSO_2(CF_2)_nSO_2F \quad\quad (II)$$

having first and second sulfonyl fluoride groups;
(b) mixing the compound of formula II with between 90-120% by mole of water; and
(c) reacting the compound according to formula II with the water to make a compound according to formula I in which the first sulfonyl fluoride group is converted to a —SO₃Y group and the second sulfonyl fluoride group remains.

In another embodiment, the current description includes a compound according to formula III:

$$R^1-CF_2-SO_2-NZ-SO_2(CF_2)_nSO_3Y \quad\quad (III)$$

where n is 2-6, Y is chosen from the group consisting of H and suitable countercations, and wherein R¹ is chosen from the group consisting of organic groups which are branched, unbranched or cyclic; saturated, unsaturated or aromatic; which optionally contain heteroatoms; which optionally are substituted; and wherein Z is chosen from the group consisting of H and suitable countercations. Methods for making a compound according to formula III are also embodied in the current description.

In another embodiment, the current description includes a polymer having pendent groups comprising groups according to formula V:

$$-(-SO_2-NZ-SO_2-R_f-)_m-(SO_3Y)_p \quad\quad (V)$$

wherein the polymer is highly fluorinated; where m is 1-6, p is at least 1, and Y is chosen from the group consisting of H and suitable countercations; wherein $R_f$ is a multivalent fluorochemical group selected from the group consisting of highly fluorinated alkyl, perfluoroalkyl, perfluoroether, perfluoroalkylamino(perfluoroalkyl)₂; which are branched, unbranched, or cyclic; and wherein Z is chosen from the group consisting of H and suitable countercations. In some embodiments, the polymer is perfluorinated. In some embodiments, the $R_f$ group is a $(-CF_2-)_n$ group, where n is 1 to 6, or n is 1 to 4, or n is 2 to 3, or n is 3. In some embodiments, m is 1. In some embodiments, p is 1 to 10.

In some embodiments, the polymer of the current description includes pendent groups according to formula VI:

$$-R^3-SO_2-NZ-SO_2(CF_2)_nSO_3Y \quad\quad (VI)$$

where n is 1-6, Y is chosen from the group consisting of H and suitable countercations, and R³ is a branched or unbranched highly fluorinated aliphatic group comprising 1-15 carbon atoms and 0-4 oxygen atoms; and wherein Z is chosen from the group consisting of H and suitable countercations. In some embodiments, the polymer is perfluorinated. In some embodiments, n is 1 to 6, or n is 1 to 4, or n is 2 to 3, or n is 3.

In another embodiment, a dispersion of the polymer of the current description in a polar solvent is described.

Another embodiment includes a polymer electrolyte composition that includes one of the polymers of the current description and a transition metal selected from the group consisting of Mn and Ce. In some embodiments of the present disclosure, a stabilizing additive may be added, non-limiting embodiments of which may include a salt or oxide of manganese or cerium, more typically an oxide, added to the polymer electrolyte prior to membrane formation.

In another aspect, articles are described herein that incorporate the compounds or compositions of the current description, including: an electrode that includes the polymer according to the current description; a polymer electrolyte membrane that includes the polymer according to the current description; and, a composite membrane comprising a porous support matrix, wherein the pores are substantially impregnated with the polymer according to the current description. The composite membrane of the current description may a Gurley value of less than 10 sec/50 cc.

In still another embodiment, the current description includes a membrane electrode assembly comprising the polymer electrolyte membrane that includes the polymer according to the current description.

In this Application:
"equivalent weight" (EW) of a polymer means the weight of polymer which will neutralize one equivalent of base;
"hydration product" (HP) of a polymer means the number of equivalents (moles) of water absorbed by a membrane per equivalent of sulfonic acid groups present in the membrane multiplied by the equivalent weight of the polymer; and
"highly fluorinated" means containing fluorine in an amount of 40 wt % or more, typically 50 wt % or more and more typically 60 wt % or more.

"bissulfonyl imide" means a —$SO_2NZSO_2$— functional group, where Z can be H or a suitable counteraction, as described below.

DETAILED DESCRIPTION

Materials taught in this disclosure may be used for fuel cell applications such as in the manufacture of fuel cell electrodes, proton exchange membranes (PEM), as catalyst additives or in tie layers designed to be thermally and chemically robust while operating within a fuel cell's harsh environment at higher temperatures and to conduct protons, with significantly higher levels of bound acidic groups, while in a low hydration state.

Materials taught in this disclosure may be used in membrane electrode assemblies (MEA's) including fuel cell MEA's. An MEA is the central element of a proton exchange membrane fuel cell, such as a hydrogen fuel cell. Fuel cells are electrochemical cells which produce usable electricity by the catalyzed combination of a fuel such as hydrogen and an oxidant such as oxygen. Typical MEA's comprise a polymer electrolyte membrane (PEM) (also known as an ion conductive membrane (ICM)) which functions as a solid electrolyte. One face of the PEM is in contact with an anode electrode layer and the opposite face is in contact with a cathode electrode layer. In typical use, protons are formed at the anode via hydrogen oxidation and transported across the PEM to the cathode to react with oxygen, causing electrical current to flow in an external circuit connecting the electrodes. Each electrode layer includes electrochemical catalysts, typically including platinum metal. The PEM forms a durable, non-porous, electrically non-conductive mechanical barrier between the reactant gases, yet it also passes $H^+$ ions readily. Gas diffusion layers (GDL's) facilitate gas transport to and from the anode and cathode electrode materials and conduct electrical current. The GDL is both porous and electrically conductive, and is typically composed of carbon fibers. The GDL may also be called a fluid transport layer (FTL) or a diffuser/current collector (DCC). In some embodiments, the anode and cathode electrode layers are applied to GDL's and the resulting catalyst-coated GDL's sandwiched with a PEM to form a five-layer MEA. The five layers of a five-layer MEA are, in order: anode GDL, anode electrode layer, PEM, cathode electrode layer, and cathode GDL. In other embodiments, the anode and cathode electrode layers are applied to either side of the PEM, and the resulting catalyst-coated membrane (CCM) is sandwiched between two GDL's to form a five-layer MEA.

In some embodiments, an MEA comprises one or more materials taught in this disclosure. In some embodiments, a PEM comprises one or more materials taught in this disclosure. In some embodiments, an MEA comprises a PEM comprising one or more materials taught in this disclosure. In some embodiments, an electrode layer comprises one or more materials taught in this disclosure. In some embodiments, an MEA comprises an electrode layer comprising one or more materials taught in this disclosure.

Proton conducting materials useful in making PEM's, electrode layers, or MEA's according to the present disclosure typically have an equivalent weight (EW) of 1200 or less, more typically 1100 or less, more typically 1050 or less, more typically 1000 or less, and in some embodiments 950 or less, 900 or less, 850 or less, or 800 or less.

In the formation of a PEM, the polymeric material can be formed into a membrane by any suitable method. The polymer is typically cast from a suspension. Any suitable casting method may be used, including bar coating, spray coating, slit coating, brush coating, and the like. Alternately, the membrane may be formed from neat polymer in a melt process such as extrusion. After forming, the membrane may be annealed, typically at a temperature of 120° C. or higher, more typically 130° C. or higher, most typically 150° C. or higher. The PEM typically has a thickness of less than 50 microns, more typically less than 40 microns, more typically less than 30 microns, and most typically about 25 microns.

In one embodiment of the present disclosure, the polymer electrolyte may contain or comprise one or more of the polyoxometalate or heteropolyacid additives described in U.S. Pat. Appl. No. 2009/0208809, the description of which is incorporated herein by reference.

In one embodiment of the present disclosure, a stabilizing additive may be added to the polymer electrolyte. In one embodiment of the present disclosure, a salt or oxide of manganese or cerium, more typically a salt, more typically manganese, is added to the acid form polymer electrolyte prior to membrane formation. Typically the salt is mixed well with or dissolved within the polymer electrolyte to achieve substantially uniform distribution. The salt may comprise any suitable anion, including chloride, bromide, nitrate, carbonate and the like. Once cation exchange occurs between the transition metal salt and the acid form polymer, it may be desirable for the acid formed by combination of the liberated proton and the original salt anion to be removed. Thus, it may be preferred to use anions that generate volatile or soluble acids, for example chloride or nitrate. Manganese cations may be in any suitable oxidation state, including $Mn^{2+}$, $Mn^{3+}$ and $Mn^{4+}$, but are most typically $Mn^{2+}$. The amount of salt added is typically between 0.001 and 0.5 charge equivalents based on the molar amount of acid functional groups present in the polymer electrolyte, more typically between 0.005 and 0.2, more typically between 0.01 and 0.15, and more typically between 0.02 and 0.1. Additional examples of suitable additives are described in U.S. Pat. No. 7,572,534 (includes Mn salts), U.S. Pat. Appl. No. 2010/0062314 (includes Mn oxides), U.S. Pat. Appl. No. 2007/0099053 (includes Ce salts), U.S. Pat. Appl. No. 2007/0099052 (includes Ce oxides), U.S. Pat. Appl. No. 2009/0208809 (includes heteropolyacids), and U.S. Pat. Appl. No. 2009/0169959 (includes combination of Mn salts and Ce oxides), the description of which are each included herein by reference.

Any suitable catalyst may be used to make electrode layers and MEA's in the practice of the present disclosure. Typically, carbon-supported catalyst particles are used. Typical carbon-supported catalyst particles are 50-90% carbon and 10-50% catalyst metal by weight, the catalyst metal typically comprising Pt for the cathode and Pt and Ru in a weight ratio of 2:1 for the anode. Typically, the catalyst is applied to the PEM or to the GDL in the form of a catalyst ink. Alternately, the catalyst ink may be applied to a transfer substrate, dried, and thereafter applied to the PEM or to the GDL as a decal. The catalyst ink typically comprises polymer electrolyte material, which may or may not be the same polymer electrolyte material which comprises the PEM. The catalyst ink typically comprises a dispersion of catalyst particles in a dispersion of the polymer electrolyte. In some embodiments of the present disclosure, a stabilizing additive could be added, typically a salt or oxide of manganese or cerium, more typically an oxide, more typically of cerium, is added to the polymer electrolyte prior to membrane formation. The ink typically contains 5-30% solids (i.e. polymer and catalyst) and more typically 10-20% solids. The electrolyte dispersion is typically an aqueous dispersion, which may additionally contain alcohols and polyalcohols such a glycerin and ethylene glycol. The water, alcohol, and polyalcohol content may be adjusted to alter rheological properties of the ink. The ink typically contains 0-50% alcohol and 0-20% polyalcohol. In addition, the ink may contain 0-2% of a suitable dispersant. The ink is typically made by stirring with heat followed by dilution to a coatable consistency.

To make an MEA or CCM, catalyst may be applied to the PEM by any suitable means, including both hand and machine methods, including hand brushing, notch bar coating, fluid bearing die coating, wire-wound rod coating, fluid bearing coating, slot-fed knife coating, three-roll coating, or decal transfer. Coating may be achieved in one application or in multiple applications.

To make an MEA, GDL's may be applied to either side of a CCM by any suitable means. Any suitable GDL may be used in the practice of the present disclosure. Typically the GDL is comprised of sheet material comprising carbon fibers. Typically the GDL is a carbon fiber construction selected from woven and non-woven carbon fiber constructions. Carbon fiber constructions which may be useful in the practice of the present disclosure may include: Toray™ Carbon Paper, SpectraCarb™ Carbon Paper, AFN™ non-woven carbon cloth, Zoltek™ Carbon Cloth, and the like. The GDL may be coated or impregnated with various materials, including carbon particle coatings, hydrophilizing treatments, and hydrophobizing treatments such as coating with polytetrafluoroethylene (PTFE).

In some embodiments, catalyst may be applied to a GDL to make a catalyst-coated backing (CCB) and CCB's may then be combined with a PEM to make an MEA. In such embodiments, catalyst may be applied to the GDL by any suitable means, including both hand and machine methods, including hand brushing, notch bar coating, fluid bearing die coating, wire-wound rod coating, fluid bearing coating, slot-fed knife coating, three-roll coating, or decal transfer. Coating may be achieved in one application or in multiple applications.

In use, the MEA according to the present typically sandwiched between two rigid plates, known as distribution plates, also known as bipolar plates (BPP's) or monopolar plates. Like the GDL, the distribution plate must be electrically conductive. The distribution plate is typically made of a carbon composite, metal, or plated metal material. The distribution plate distributes reactant or product fluids to and from the MEA electrode surfaces, typically through one or more fluid-conducting channels engraved, milled, molded or stamped in the surface(s) facing the MEA(s). These channels are sometimes designated a flow field. The distribution plate may distribute fluids to and from two consecutive MEA's in a stack, with one face directing fuel to the anode of the first MEA while the other face directs oxidant to the cathode of the next MEA (and removes product water), hence the term "bipolar plate." Alternately, the bipolar plate may have one face directing fuel or oxidant to an MEA while the other face includes channels which conduct coolant. Alternately, the distribution plate may have channels on one side only, to distribute fluids to or from an MEA on only that side, which may be termed a "monopolar plate." The term bipolar plate, as used in the art, typically encompasses monopolar plates as well. A typical fuel cell stack comprises a number of MEA's stacked alternately with distribution plates.

II. Compounds

In one embodiment, the present disclosure provides a compound according to formula III:

$$R^1-CF_2-SO_2-NZ-SO_2(CF_2)_n SO_3 Y \quad (III)$$

where $R^1$ is an organic group, and where n is 2-6, Y is hydrogen or a suitable countercation. In general, $R^1$ is chosen from the group consisting of organic groups which are branched, unbranched or cyclic; saturated, unsaturated or aromatic, which optionally contain heteroatoms; which optionally are substituted. In non-limiting embodiments, optional substitutions may include F, Cl, Br, and/or I. In some embodiments, n is 1. In some embodiments, n is 2. In some embodiments, n is 3. In some embodiments, n is 4. In some embodiments, n is 5. In some embodiments, n is 6. In some embodiments, Z is H. In some embodiments, Z is a suitable countercation and the N bears a negative charge. In some embodiments, Y is H. In some embodiments, Y is a suitable countercation and the $SO_3$ group bears a negative charge.

Suitable countercations may include monovalent or polyvalent cations. In some embodiments, suitable countercations are monovalent cations. In some embodiments, suitable countercations are selected from H+ and cations of alkali metals. In some embodiments, suitable countercations are selected from monovalent or polyvalent cations of alkaline earths. In some embodiments, suitable countercations may be alkylammonium cations, including triethylammonium cations.

In some embodiments, $R^1$ may be a branched or unbranched highly fluorinated fluoroalkyl or fluoroether group comprising 1-15 carbon atoms and 0-4 oxygen atoms. In some embodiments, $R^1$ may be a branched or unbranched perfluoroalkyl or perfluoroether group comprising 1-15 carbon atoms and 0-4 oxygen atoms.

Non-limiting examples of perfluorinated $R^1$ groups may include the following:

$F(CF_2)_n$— where n is 1, 2, 3, 4, 5, 6, 7, 8, 9, 10, 11, 12, 13, 14 or 15;

$F(-CF_2 CF(CF_3)-)_n$ where n is 1, 2, 3, 4, or 5;

$F(-CF(CF_3)CF_2-)_n$ where n is 1, 2, 3, 4, or 5;

$F(-CF_2 CF(CF_3)-)_n-CF_2-$ where n is 1, 2, 3, 4, or 5.

Non-limiting examples of perfluoroether $R^1$ groups may include the following:

$CF_2=CF-(-O-CF_2 CF_2-)_n$ where n is 1, 2, 3, 4, 5, 6 or 7;

$CF_2=CF-(-O-CF_2 CF_2 CF_2-)_n$ where n is 1, 2, 3, 4, or 5;

$CF_2=CF-(-O-CF_2 CF_2 CF_2 CF_2-)_n$ where n is 1, 2 or 3;

$CF_2=CF-(-O-CF_2 CF(CF_3)-)_n$ where n is 1, 2, 3, 4, or 5;

$CF_2=CF-(-O-CF_2 CF(CF_2 CF_3)-)_n$ where n is 1, 2 or 3;

$CF_2=CF-(-O-CF(CF_3)CF_2-)_n$ where n is 1, 2, 3, 4 or 5;

$CF_2=CF-(-O-CF(CF_2 CF_3)CF_2-)_n$ where n is 1, 2 or 3;

$CF_2=CF-(-O-CF_2 CF(CF_3)-)_n-O-CF_2 CF_2-$ where n is 1, 2, 3 or 4;

$CF_2=CF-(-O-CF_2CF(CF_2CF_3)-)_n-O-CF_2CF_2-$ where n is 1, 2 or 3;

$CF_2=CF-(-O-CF(CF_3)CF_2-)_n-O-CF_2CF_2-$ where n is 1, 2, 3 or 4;

$CF_2=CF-(-O-CF(CF_2CF_3)CF_2-)_n-O-CF_2CF_2-$ where n is 1, 2 or 3;

$CF_2=CF-O-(CF_2)_n-$ where n is 1, 2, 3, 4, 5, 6, 7, 8, 9, 10, 11, 12, 13 or 14.

In some embodiments, $R^1$ may be a group according to formula XIII:

$$CF_2=CF-O-R^2- \qquad (XIII)$$

wherein $R^2$ may be selected from groups that are branched, unbranched or cyclic; saturated, unsaturated or aromatic, which optionally contain heteroatoms; which optionally are substituted.

Composition:

In one embodiment, the present disclosure provides a composition comprising any of the compounds according to formula III:

$$R^1-CF_2-SO_2-NX-SO_2(CF_2)_nSO_3Y \qquad (III)$$

as described above. In some embodiments, the composition contains substantially no compound according to formula IV:

$$R^1-CF_2-SO_2-NX-SO_2(CF_2)_nSO_2-NX-SO_2-CF_2-R^1 \qquad (IV)$$

where n is 2-6 and wherein each $R^1$ is independently chosen from the $R^1$ groups as described above, and wherein each X is independently chosen from the group consisting of H and suitable countercations, as described above.

Polymer:

The polymer to be functionalized as described in the methods section comprises a backbone, which may be branched or unbranched but is typically unbranched. The backbone is fluorinated, typically highly fluorinated, and more typically perfluorinated. The backbone may comprise units derived from tetrafluoroethylene (TFE), i.e., typically $-CF_2-CF_2-$ units, and units derived from co-monomers, typically including at least one according to the formula $CF_2=CY-R^{10}$ where Y is typically F but may also be $CF_3$, and where $R^{10}$ is a first pendant group which includes a group according to the formula $-SO_2X$ wherein X is selected from F, Cl, Br, I, $-OH$ or $-O-SO_2R^5$ wherein $R^5$ is an aliphatic group containing 1-18 carbon atoms which may be substituted. Where $-SO_2X$ is a sulfonyl halide, X is most typically F. In an alternative embodiment, first pendant groups $R^{10}$ may be added to the backbone by grafting. Typically, first pendant groups $R^{10}$ are highly fluorinated and more typically perfluorinated. $R^{10}$ may be aromatic or non-aromatic. Typically, $R^{10}$ is $-R^{11}-SO_2X$, where $R^{11}$ is a branched or unbranched perfluoroalkyl or perfluoroether group comprising 1-15 carbon atoms and 0-4 oxygen atoms. $R^{11}$ is typically $-O-R^{12}-$ wherein $R^{12}$ is a branched or unbranched perfluoroalkyl or perfluoroether group comprising 1-15 carbon atoms and 0-4 oxygen atoms. $R^{11}$ is more typically $-O-R^{13}-$ wherein $R^{13}$ is a perfluoroalkyl group comprising 1-15 carbon atoms. Examples of $R^{11}$ include:

$-(CF_2)_n-$ where n is 1, 2, 3, 4, 5, 6, 7, 8, 9, 10, 11, 12, 13, 14 or 15

$(-CF_2CF(CF_3)-)_n$ where n is 1, 2, 3, 4, or 5

$(-CF(CF_3)CF_2-)_n$ where n is 1, 2, 3, 4, or 5

$(-CF_2CF(CF_3)-)_n-CF_2-$ where n is 1, 2, 3 or 4

$(-O-CF_2-)_n$ where n is 1, 2, 3, 4, 5, 6 or 7

$(-O-CF_2CF_2-)_n$ where n is 1, 2, 3, 4, or 5

$(-O-CF_2CF_2CF_2-)_n$ where n is 1, 2 or 3

$(-O-CF_2CF(CF_3)-)_n$ where n is 1, 2, 3, 4, or 5

$(-O-CF_2CF(CF_2CF_3)-)_n$ where n is 1, 2 or 3

$(-O-CF(CF_3)CF_2-)_n$ where n is 1, 2, 3, 4 or 5

$(-O-CF(CF_2CF_3)CF_2-)_n$ where n is 1, 2 or 3

$(-O-CF_2CF(CF_3)-)_n-O-CF_2CF_2-$ where n is 1, 2, 3 or 4

$(-O-CF_2CF(CF_2CF_3)-)_n-O-CF_2CF_2-$ where n is 1, 2 or 3

$(-O-CF(CF_3)CF_2-)_n-O-CF_2CF_2-$ where n is 1, 2, 3 or 4

$(-O-CF(CF_2CF_3)CF_2-)_n-O-CF_2CF_2-$ where n is 1, 2 or 3

$-O-(CF_2)_n-$ where n is 1, 2, 3, 4, 5, 6, 7, 8, 9, 10, 11, 12, 13 or 14

$R^{10}$ is typically $-O-CF_2CF_2CF_2CF_2-SO_2X$ or $-O-CF_2-CF(CF_3)-O-CF_2-CF_2-SO_2X$ and most typically $-O-CF_2CF_2CF_2CF_2-SO_2X$. The $-SO_2X$ group is most typically $-SO_2F$ during polymerization, i.e., X is F. The $-SO_2X$ group is typically converted to $-SO_3H$ at some point prior to use of the fluoropolymer as an polymer electrolyte. The fluoromonomer providing first side group $R^{10}$ may be synthesized by any suitable means, including methods disclosed in U.S. Pat. No. 6,624,328, which is incorporated herein by reference.

The polymer may be made by any suitable method, including emulsion polymerization, extrusion polymerization, polymerization in supercritical carbon dioxide, solution or suspension polymerization, and the like, including methods disclosed in U.S. Pat. No. 7,071,271, which is incorporated herein by reference, and references cited therein.

Where the $-SO_2X$ group is $-SO_2F$ during polymerization, some of the $-SO_2F$ groups may be converted to more reactive groups prior to further reactions of the present disclosure, such as $-SO_2Cl$, $-SO_2Br$, $-SO_2I$ or $-O-SO_2R^2$ wherein $R^2$ is an aliphatic group containing 1-18 carbon atoms which may be substituted, more typically containing 1-8 carbon atoms, and most typically methyl or ethyl. Typically, between 1 and 50% of $-SO_2F$ groups are converted to more reactive groups. $-SO_2F$ groups may be converted by any suitable method. $-SO_2F$ groups may be converted to $-SO_2Cl$ groups by any suitable method. In one such method, $-SO_2F$ groups are reduced to $-SO_2H$ by use of a suitable reducing agent, such as a hydrazine or mercaptan such as mercaptoethanol, and subsequently converted to $-SO_2Cl$ with a hypochloride. In another such method, $-SO_2F$ groups may be converted to $-SO_2Cl$ groups by reaction with oxalyl chloride in dry toluene with pyridine catalyst. $-SO_2F$ groups may be converted to $-O-SO_2R^2$ groups by any suitable method. In one such method, $-SO_2F$ groups are converted by exchange with $R^2-SO_2-O-SO_2R^2$, e.g. $CH_3-SO_2-)-SO_2-CH_3$. In another such method, $-SO_2F$ groups are converted by reaction with $R^2-SO_3H$ and $P_2O_5$.

In one embodiment of the present disclosure, the polymer additionally comprises second pendent groups which include groups $-Ar$, wherein each Ar is selected independently from aromatic groups containing 6-24 carbon or nitrogen atoms and wherein each Ar may be substituted. Typical Ar groups include phenyl, naphthyl, anthracyl, phenanthracyl, biphenyl, terphenyl, fluoryl, indyl, fluoranthyl, pyridyl, puryl and the like. When substituents are present, they are typically electron donating substituents, such as alkoxy, hydroxy, amine, alkyl and the like. The second pendent groups may be introduced into the polymer by ter-polymerization with monomers such as $CF_2=CY-R^{20}$ where Y is typically F but may also be $CF_3$, and where $R^{20}$ is the second pendant group. In an alternative embodiment, first pendant groups $R^{20}$ may be added to the backbone by grafting. Second pendent groups $R^{20}$ may be according to the formula $-R^{11}-Ar$, where $R^{11}$ is as described above. In some embodiments of the invention, the polymer is optionally crosslinked by joining first and second pendent groups, as described in U.S. Pat. No. 7,060,756 which is incorporated herein by reference. The second pendent groups are present in the polymer in a numerical (molar) amount that is less than the amount of the first pendent groups, typically less than 90% relative to the amount of the first pendent groups and more typically less than 50%.

In one embodiment, the present disclosure provides a polymer having pendent groups comprising groups according to formula VI:

$$-R^3-SO_2-NZ-SO_2(CF_2)_nSO_3Y \qquad (VI)$$

where n is 1-6 and Y is hydrogen or an alkali metal; and wherein Z is chosen from the group consisting of H and suitable countercations. In some embodiments, n is 1. In some embodiments, n is 2. In some embodiments, n is 3. In some embodiments, n is 4. In some embodiments, n is 5. In some embodiments, n is 6. In some embodiments, Z is H. In some embodiments, Z is a suitable countercation and the N bears a negative charge. In some embodiments, Y is H. In some embodiments, Y is a suitable countercation and the $SO_3$ group bears a negative charge.

Suitable countercations may include monovalent or polyvalent cations. In some embodiments, suitable countercations are monovalent cations. In some embodiments, suitable countercations are selected from H+ and cations of alkali metals. In some embodiments, suitable countercations are selected from monovalent or polyvalent cations of alkaline earths. In some embodiments, suitable countercations are alkylammonium cations, including triethylammonium cations.

In some embodiments, $R^3$ is $-O-R^4-$ wherein $R^4$ is a branched or unbranched highly fluorinated aliphatic group comprising 1-15 carbon atoms and 0-4 oxygen atoms. In some embodiments, $R^3$ is typically perfluoroalkyl or perfluoroether group comprising 1-15 carbon atoms and 0-4 oxygen atoms. In some embodiments, $R^3$ is $-O-R^4-$ wherein $R^4$ is a branched or unbranched perfluoroalkyl group comprising 1-15 carbon atoms. Examples of $R^3$ may include:

- $-(CF_2)_n-$ where n is 1, 2, 3, 4, 5, 6, 7, 8, 9, 10, 11, 12, 13, 14 or 15;
- $(-CF_2CF(CF_3)-)_n$ where n is 1, 2, 3, 4, or 5;
- $(-CF(CF_3)CF_2-)_n$ where n is 1, 2, 3, 4, or 5;
- $(-CF_2CF(CF_3)-)_n-CF_2-$ where n is 1, 2, 3 or 4;
- $(-O-CF_2CF_2-)_n$ where n is 1, 2, 3, 4, 5, 6 or 7;
- $(-O-CF_2CF_2CF_2-)_n$ where n is 1, 2, 3, 4, or 5;
- $(-O-CF_2CF_2CF_2CF_2-)_n$ where n is 1, 2 or 3;
- $(-O-CF_2CF(CF_3)-)_n$ where n is 1, 2, 3, 4, or 5;
- $(-O-CF_2CF(CF_2CF_3)-)_n$ where n is 1, 2 or 3;
- $(-O-CF(CF_3)CF_2-)_n$ where n is 1, 2, 3, 4 or 5;
- $(-O-CF(CF_2CF_3)CF_2-)_n$ where n is 1, 2 or 3;
- $(-O-CF_2CF(CF_3)-)_n-O-CF_2CF_2-$ where n is 1, 2, 3 or 4;
- $(-O-CF_2CF(CF_2CF_3)-)_n-O-CF_2CF_2-$ where n is 1, 2 or 3;
- $(-O-CF(CF_3)CF_2-)_n-O-CF_2CF_2-$ where n is 1, 2, 3 or 4;
- $(-O-CF(CF_2CF_3)CF_2-)_n-O-CF_2CF_2-$ where n is 1, 2 or 3;
- $-O-(CF_2)_n-$ where n is 1, 2, 3, 4, 5, 6, 7, 8, 9, 10, 11, 12, 13 or 14.

In polymers of the current description that include pendent groups comprising groups according to formula VI, acid-functional pendant groups typically are present in an amount sufficient to result in a hydration product (HP) of greater than 15,000, more typically greater than 18,000, more typically greater than 22,000, and most typically greater than 25,000. In general, higher HP correlates with higher ionic conductance.

The acid-functional pendant groups typically are present in an amount sufficient to result in an equivalent weight (EW) of less than 1200, more typically less than 1100, and more typically less than 1000, and more typically less than 900.

III. Methods of Making

Method of Making Compound of Formula (I)

The current description provides a method of making a compound of formula (I)

$$FSO_2(CF_2)_nSO_3Y \qquad (I)$$

where Y may be H or a suitable countercation, and where n is 1-6, comprising the step of reacting a compound according to formula II $$FSO_2(CF_2)_nSO_2F \qquad (II)$$

with between 80-120% by mole of water. In some embodiments, n is 1-4. In some embodiments, n is 2-3. In some embodiments, n is 3.

In some embodiments, the method of the current description includes steps of:

(a) providing a compound according to formula II:

$$FSO_2(CF_2)_nSO_2F \qquad (II)$$

having first and second sulfonyl fluoride groups;

(b) mixing the compound of formula II with between 90-120% by mole of water; and (c) reacting the compound according to formula II with the water to make a compound according to formula I in which the first sulfonyl fluoride group is converted to a $-SO_3Y$ group and the second sulfonyl fluoride group remains.

The $-SO_3Y$ group of the current description may be referred to as a sulfonic acid group when Y is H, or sulfonate group when Y is a suitable countercation.

As described above, suitable countercations may include monovalent or polyvalent cations. In some embodiments, suitable countercations are monovalent cations. In some embodiments, suitable countercations are selected from H+ and cations of alkali metals. In some embodiments, suitable countercations are selected from monovalent or polyvalent cations of alkaline earths. In some embodiments, suitable countercations may be alkylammonium cations, including triethylammonium cations.

The formation of several compounds of formula I (where n is 2-4) by ring-opening of anhydride compounds with fluoride salts has been described in U.S. Pat. No. 5,011,983 (Behr), incorporated herein by reference. The presently described method has an advantage of eliminating the need to form cyclic anhydride compounds from compounds of formula II, such cyclic anhydrides being otherwise difficult to obtain. The present method also provides reaction mixtures that conveniently may be used for making derivates, without requiring isolation of the compounds of formula I.

The disulfonyl fluoride compounds of formula II may be represented as in formulas IIa-f. Compounds of formulas IIa-f may be prepared by a variety of known methods, including for example the methods described in U.S. Pat. No. 2,732,398 (Brice et al.), incorporated herein by reference in its entirety, or other methods known in the art.

$$FSO_2-CF_2-SO_2F \qquad (IIa)$$

$$FSO_2(CF_2)_2SO_2F \qquad (IIb)$$

$$FSO_2(CF_2)_3SO_2F \qquad (IIc)$$

$$FSO_2(CF_2)_4SO_2F \quad (IId)$$

$$FSO_2(CF_2)_5SO_2F \quad (IIe)$$

$$FSO_2(CF_2)_6SO_2F \quad (IIf)$$

In some embodiments, reaction of a compound according to formula II with water (i.e., hydrolysis) may be carried out in the absence of added solvent. In some embodiments, the amount of water for the hydrolysis reaction may be in the range of about 80% by mole to 120% by mole relative to the compound of formula II. As the amount of water relative to compound of formula II increases beyond 120% by mole, over-hydrolysis to a bis-sulfonic acid compound may occur (i.e., the second sulfonyl group may be hydrolyzed to some extent). In some embodiments, the level of hydrolysis of the second sulfonyl fluoride group relative to hydrolysis of the first sulfonyl fluoride group may be less than 20% by mole, or less than 10% by mole, or less than 5% by mole. If insufficient water is present, incomplete hydrolysis of the first sulfonyl fluoride group may result in residual compound of formula II in the reaction mixture. In some embodiments, the level of residual compound of formula II relative to compound of formula I may be less than 20% by mole, or less than 10% by mole, or less than 5% by mole. When a solvent other than water is used in the reaction, the amount of water present in the solvent may need to be taken into account in determining the total amount of water being added.

When no additional solvent is included, a biphasic mixture of water and the compound of formula II may form. Whether or not a solvent is included, the reaction of a compound of formula II with water is typically performed in the presence of a suitable base. The biphasic mixture may be treated with a suitable base to aid the hydrolysis reaction. Non-limiting examples of suitable bases may include aprotic amine bases like triethylamine or N,N-diisopropylethylamine. The amount of base used is typically at least 80% by mole relative to the compound of formula II, although higher % by mole values may also be used, including 100% by mole, 200% by mole, and 300% by mole.

In some embodiments, the reaction of the compound according to formula II may be carried out in the presence of an additional solvent, including a suitable polar aprotic solvent that is miscible with water and miscible with the compound according to formula II. Non-limiting examples of suitable polar aprotic solvents may include acetone, acetonitrile, tetrahydrofuran, and combinations thereof.

Suitable temperatures for the described hydrolysis of a compound of formula II to form a compound of formula I may include temperatures at or below about 25° C.

When the hydrolysis of a compound of formula II to a compound of formula I is carried out in a suitable polar aprotic solvent, the resulting mixture of a compound of formula I in solvent may be used for further reactions with sulfonamides, amines, or other organic nucleophiles, without isolation of the compound of formula I. In some embodiments, reaction of a compound of formula I with a sulfonamide may include the formation of compounds of formula III:

$$R^1—CF_2—SO_2—NZ—SO_2(CF_2)_nSO_3Y \quad (III)$$

where n is 2-6, Y is chosen from the group consisting of H and suitable countercations, and wherein $R^1$ is chosen from the group consisting of organic groups which are branched, unbranched or cyclic; saturated, unsaturated or aromatic, which optionally contain heteroatoms; which optionally are substituted; and where Z is chosen from the group consisting of H and suitable countercations.

In some embodiments, the method of the current description includes the preparation of a compound of formula III by reaction of a compound of formula I with a sulfonamide compound while minimizing the formation of compounds of formula IV. In some embodiments, the formation of a compound for formula IV relative to the formation of compound of formula III is less than 10% by mole, or less than 5% by mole, or less than 2% by mole.

$$R^1—CF_2—SO_2—NZ—SO_2(CF_2)_nSO_2—NZ—SO_2—CF_2—R^1 \quad (IV)$$

In some embodiments, a method of making a compound according to formula III includes the step of reacting a compound comprising a group according to formula XI:

$$R^1—CF_2—SO_2—NH_2 \quad (XI)$$

with a compound according to formula II:

$$FSO_2(CF_2)_nSO_2F \quad (II)$$

where n is 2-6 and wherein $R^1$ is chosen from the group consisting of groups which are branched, unbranched or cyclic; saturated, unsaturated or aromatic, which optionally contain heteroatoms; which optionally are substituted.

In some embodiments, a method of making a compound according to formula III includes the step of reacting a compound comprising a group according to formula XII:

$$R^1—CF_2—SO_2F \quad (XII)$$

with a compound according to formula IX:

$$HSO_3(CF_2)_n—SO_2—NH_2 \quad (IX)$$

where n is 2-6 and wherein $R^1$ is chosen from the group consisting of groups which are branched, unbranched or cyclic; saturated, unsaturated or aromatic, which optionally contain heteroatoms; which optionally are substituted.

Method of Making Polymer having Pendant Groups of Formula VI.

In some embodiments, methods for making polymers having pendant groups of formula VI (described above) may include the step of reacting a polymer having pendent groups according to formula VII:

$$—CF_2—SO_2—NH_2 \quad (VII)$$

with a compound according to formula II:

$$FSO_2(CF_2)_nSO_2F \quad (II)$$

where n is 1-6.

Polymers having sulfonamide pendent groups according to formula VII may be prepared from polymers having —$CF_2$—$SO_2$—X groups, according to methods described in U.S. Pat. Appl. No. 2009/0269644, which is incorporated herein by reference.

In other embodiments, methods for making polymers having pendant groups of formula VI may include the step of reacting a polymer having pendent groups according to formula VIII:

$$—CF_2—SO_2F \quad (VIII)$$

with a compound according to formula IX:

$$HSO_3(CF_2)_n—SO_2—NH_2 \quad (IX)$$

where n is 1-6. Compounds according to formula IX may be synthesized according to the methods described in U.S. Pat. No. 4,329,478 (Behr), U.S. Pat. No. 4,386,214 (Behr), and U.S. Pat. No. 4,423,197 (Behr), the disclosures of which are each incorporated herein by reference, or alternatively may prepared by reaction of a compound of formula II with ammonia.

In additional embodiments, polymers of formula VI may be prepared by iteratively converting a pendant sulfonyl fluoride group to a sulfonamide, followed by reaction with a compound of formula II to form a bissulfonyl imide functional group and have a new sulfonyl fluoride group remaining at the end of the pendant group. Hydrolysis of the terminal sulfonyl fluoride group would then provide an $SO_3H$ group at the end of the pendant group.

Articles

In some embodiments, polymeric proton conducting materials of the current description may be suitable for use in the preparation of articles including electrodes, polymer electrolyte membranes, and membrane electrode assemblies useful in fuel cells.

In a further embodiment, polymeric proton conducting materials of the current description may be imbibed into a porous supporting matrix, typically in the form of a thin membrane having a thickness of 90 microns or less, more typically 60 microns or less, and most typically 30 microns or less. In some embodiments, the porous supporting matrix has a microstructure of micropores, and the microstructure of micropores is substantially impregnated with the polymeric proton conducting materials of the current description. Any suitable method of imbibing the polymer into the pores of the supporting matrix may be used, including overpressure, vacuum, wicking, immersion, and the like. Any suitable supporting matrix may be used. Typically the supporting matrix is electrically non-conductive. Typically, the supporting matrix is composed of a fluoropolymer, which is more typically perfluorinated. Typical matrices include porous polytetrafluoroethylene (PTFE), such as biaxially stretched PTFE webs. Additional embodiments may be found in U.S. Pat. Nos. RE37,307, RE37,656, RE37,701, and 6,254,978, the disclosures of which are incorporated herein by reference.

For embodiments where the polymeric proton conducting materials of the current description is imbibed into a porous supporting matrix, a Gurley Porosity value may be measured as a measure of the resistance to gas flow of a membrane, expressed as the time necessary for a given volume of gas to pass through a standard area of the membrane under standard conditions, as specified in ASTM D726-58, Method A. In some embodiments, a composite membrane with a Gurley value less than approximately 10 sec/50 cubic centimeters (cc) may be useful as a component in a fuel cell.

The scope of this disclosure should not be restricted solely to polymers electrolytes or fuel cell applications, as one could envision applications outside of fuel cell use.

Objects and advantages of this disclosure are further illustrated by the following examples, but the particular materials and amounts thereof recited in these examples, as well as other conditions and details, should not be construed to unduly limit this disclosure.

EXAMPLES

Test Methods
Proton Conductivity Test:

Conductivity measurements were done using a standard, in-plane, 4 point probe conductivity apparatus with platinum electrodes. The cell is electrically connected to a potentiostat (Model 273, Princeton Applied Research, Oak Ridge, Tenn.) and an Impedance/Gain Phase Analyzer (SI 1260, Schlumberger). AC impedance measurements were performed using ZPLOT and ZVIEW software (Scribner Associates Inc., Southern Pines, N.C.). Temperature and relative humidity (RH) was controlled with a constant humidity oven (Model 1000H from TestEquity, Moorpark, Calif.). In the test method, an initial condition of 70% RH at a set temperature of 80° C. was selected, and then the % RH was stepped down incrementally to 25% RH, and then stepped back up to 90% RH. Each condition was maintained for 90 minutes.

Swell/Water Uptake Test:

Membrane sample strips (one centimeter wide) were weighed and initial lengths were measured. The samples were then boiled in water for 3 hours, removed from boiling water and then removed from heat. The samples were placed on a wet glass plate and the length of the sample was measured. The sample was then patted dry on a paper towel and weighed. The % Swell was calculated as 100×[(final length)−(initial length)/(initial length)]. The % Uptake was calculated as 100×[(final mass)−(initial mass)/(initial mass)]. A 'Lambda' value of the number of water molecules per sulfonic acid group was also calculated based on the EW of the conductive polymer.

Materials:

Unless otherwise noted, all reagents were obtained or are available from Aldrich Chemical Co., Milwaukee, Wis., or may be synthesized by known methods.

1,1,2,2,3,3-Hexafluoro-propane-1,3-disulfonyl difluoride (FW 316.15) may be prepared according to U.S. Pat. No. 2,732,398.

KAPTON™ is a polyimide film available from E. I. du Pont de Nemours and Company (Wilmington, Del.)

Example 1

Hydrolysis of
1,1,2,2,3,3-Hexafluoro-propane-1,3-disulfonyl
difluoride

Water (0.279 g, 16 mmol) was added to a 3 neck flask containing perfluoropropane disulfonyl fluoride (PFPDSF, 5.05 g, 16 mmol). The biphasic mixture was cooled to 5° C., under a nitrogen blanket, in an ice bath. A mixture of triethylamine (TEA; 5.05 g, 50 mmol) and acetonitrile (4.9 g) was then added dropwise, with stirring, over 15 minutes. $^{19}F$ NMR showed conversion to perfluoropropane mono-sulfonic acid mono-sulfonyl fluoride (i.e., 1,1,2,2,3,3-hexafluoro-3-fluorosulfonyl-propane-1-sulfonic acid, the compound of formula I with n=3), having signals at 43.8 ppm, −106.9 ppm, −115.1 ppm and −119.3 ppm. A small amount (ca. 4%) of perfluoropropane disulfonic acid byproduct was also present, with peaks at −114.6 ppm and −119.7 ppm.

Example 2

Hydrolysis of
1,1,2,2,3,3-Hexafluoro-propane-1,3-disulfonyl
difluoride, Using Acetone Solvent 1,1,2,2,3,3-Hexafluoro-propane-1,3-disulfonyl difluoride (0.91 g, 2.9 mmol) was added to a mixture of 0.76 g of acetone-$d_6$ and water (0.035 g, 1.9 mmol). The vial was cooled to 5° C. and then triethylamine (0.44 g, 4.3 mmol) was added. After 1 hour, $^{19}F$ NMR showed absence of starting material signals (46.3 ppm, −108.7 ppm and −119.5 ppm), and the appearance of signals consistent with the formation of perfluoropropane mono-sulfonic acid mono-sulfonyl fluoride (43.8 ppm, −107.1 ppm, −115.3 ppm and −119.1 ppm). A small amount (ca. 5%) of 1,1,2,2,3,3-hexafluoro-propane-1,3-disulfonic acid byproduct was also evident (signals at −114.5 ppm and −119.3 ppm). This solution could be used as such in subsequent reactions.

Preparative Example 1 (PE1)

Sulfonamide Polymer

The polymer used in this preparative example was a copolymer of tetrafluoroethylene (TFE) and $FSO_2$—$CF_2CF_2CF_2CF_2$—O—$CF=CF_2$, described in U.S. patent application Ser. No. 10/322,254, U.S. Pat. No. 6,624,328, and U.S. Pat. No. 7,348,088, each of which are incorporated herein by reference. About 23 g of the polymer was placed into a 600 mL Parr® bomb (Parr Instrument Company, Moline, Ill.) along with 150 g of acetonitrile. The Parr® bomb was sealed, evacuated and chilled to −20 C, with low agitation. Ammonia was added to 40 psig and the mixture was kept below 5° C. for 6 hours, and was then allowed to warm up to room temperature and continue agitating overnight. The Parr bomb was opened and the grey solid polymer was removed and subsequently dissolved in a mixture of 108 g of methanol and 20 g of deionized (DI) water with modest warming. Lithium hydroxide monohydrate (5.7 g, FW 41.97, 0.136 mol) and 40 g of DI water was added to the clear colorless solution and roller mixed with heating. The solution was then acidified to about pH 3 by treatment with Amberlite IR-120 ion exchange beads (acidified and rinsed) a total of 6 times. An $^{19}F$ NMR spectrum of the acidified solution showed a —$CF_2C\underline{F}_2SO_2NH_2$ peak at −115.0 ppm in a 12:1 ratio with a —$CF_2C\underline{F}_2SO_3H$ peak at −115.7 ppm. The solution was dried at 60° C. overnight, resulting in 12.1 g of light yellow, cloudy solid.

Example 3

Reaction of $FSO_2(CF_2)_3SO_3H$ with Polymer having Pendant Sulfonamide Groups A 600 ml Parr® reactor (Parr Instrument Company, Moline, Ill.) was heated to 70° C. under vacuum, filled with nitrogen gas and cooled to room temperature. A 836EW perfluorinated polymer having pendant sulfonamide functional groups (prepared according to the process described for PE1) was then added, at roughly 8% solids, as 55.5 g of an anhydrous $CH_3CN$ solution. The reaction mixture from Example 1 (ca. 14.5 g) was transferred into the reactor, which was then sealed and partially evacuated. Triethylamine (5.2 g, 51 mmol) was pulled into the closed vessel, and the reactor was then heated to 80° C. while stirring at 200 rpm. After 20 hours, the reactor was opened and the polymer solid was analyzed using $^{19}F$ NMR. New peaks at −112.9, −113.6 demonstrated the formation of a bis-sulfonylimide group (—C$\underline{F}_2SO_2NHSO_2C\underline{F}_2CF_2CF_2SO_3H$, or triethylamine salt thereof), consistent with attachment of the perfluoropropane mono sulfonic acid mono sulfonyl fluoride small molecule to the polymer through a reaction with the sulfonamide group.

Example 4

PEM Polymer and Membrane Preparation

A sample (17 g, 21 mmol) of a 812 EW substantially sulfonamide(triethylamine salt) perfluorinated polymer prepared according to PE1 was dissolved with heating in 279 g of dry acetonitrile, in a single neck flask. A portion of 1,1,2,2,3,3-hexafluoro-propane-1,3-disulfonyl difluoride (PFPDSF, 41.3 g, 130 mmol) was added, followed by dropwise addition of triethylamine (40.8 g, 400 mmol). After several hours, $^{19}F$ NMR showed no starting PFPDSF present, and more PFPDSF (11.5 g, 36 mmol) was added to react with residual sulfonamide groups. The solution was concentrated under reduced pressure at 43° C. to remove volatile materials. Additional acetonitrile, 2M LiOH (4 g, 8 mmol) and water (5 g, 280 mmol) were added to the flask and again concentrated under reduced pressure. Acetonitrile and acetone were added and heated to 55° C. to give a solution. Triethylamine (4 g, 40 mmol) was added to increase the pH to 10, and heating was continued for 1 hour. More 2M LiOH (8.5 g, 17 mmol) was added and the mixture was concentrated under reduced pressure to leave a brown solid. The solid was extracted with a 90:10 mixture of tetrahydrofuran (THF) and water, and then was dissolved in methanol/water/acetone (68:8:24) with heating. More 2M LiOH (18 g, 36 mmol) was added and the mixture was again concentrated under reduced pressure to leave a solid. The solid was extracted with a 90:10 mixture of THF and water, and then with a 90:10 mixture of THF and ethanol. The solid was dissolved in acetone and ethanol, and 2M LiOH (22 g, 44 mmol) and water (6 g) were added, and the mixture was partially concentrated under reduced pressure. The polymer was precipitated with THF/heptane, and then redissolved in acetone/water; this precipitation treatment was repeated twice. The precipitated solid was then dried (130° C. oven), resulting in 11.6 g of material. The polymer was dissolved in a mixture of ethanol (90 g), acetone (10 g) and 2M LiOH (5 g, 10 mmol) with heat to obtain a gel-free, low viscosity solution.

A portion of the solution was exposed to Amberlite IR-120 ion exchange beads (acidified and rinsed) twice to reduce the pH to about 1.5. The solution was dried at 65° C. overnight, resulting in 7.15 g of dark brown solid. An $^{19}F$ NMR spectrum of the solid was consistant with substantially monosulfonyl imide product and little perfluoropropane disulfonic acid. A methanol/water solution (84:16) containing the polymer at 16% solids was coated on KAPTON™ film and oven dried at 130° C. for 30 minutes and then at 180° C. for 10 minutes to produce a 1 mil proton exchange membrane.

For comparison with the polymeric material and membrane obtained in Example 4, several Comparative Example (CE) PEM samples were prepared according to the method described in U.S. Pat. No. 7,348,088, the description of which is incorporated herein by reference, including PEMs with the following EW values:

| Comparative Example | EW |
|---|---|
| CE 1 | 700 |
| CE 2 | 825 |
| CE 3 | ~900 |
| CE 4 | 1000 |
| CE 5 | ~1100 |

Figure 1:
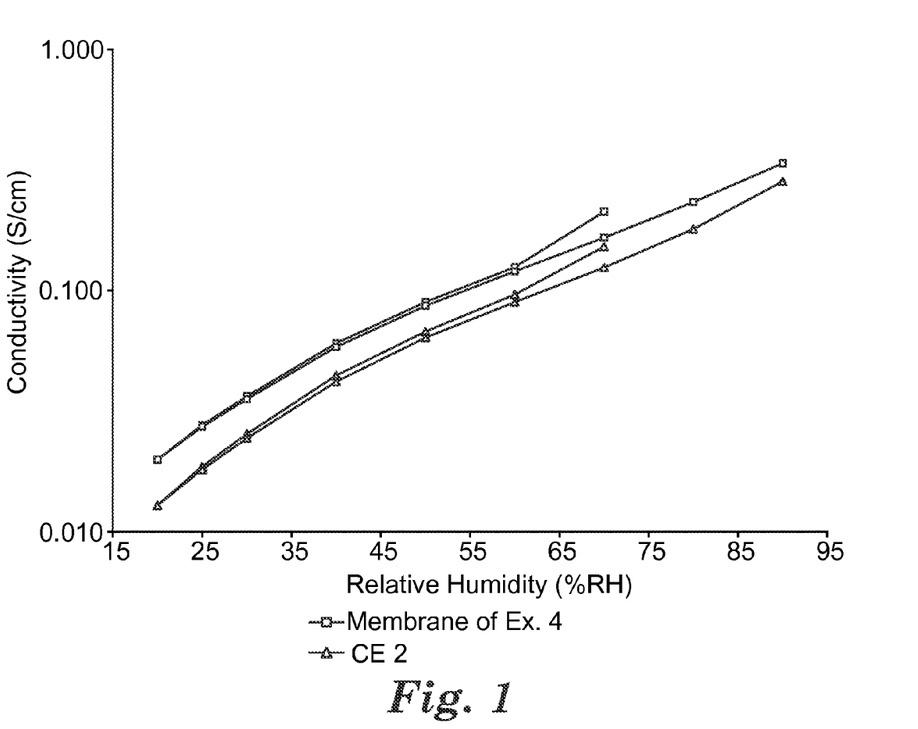
FIG. 1 is a graph of proton conductivity measurements at various levels of relative humidity for the proton exchange membrane described in Example 4.
Figure 2:
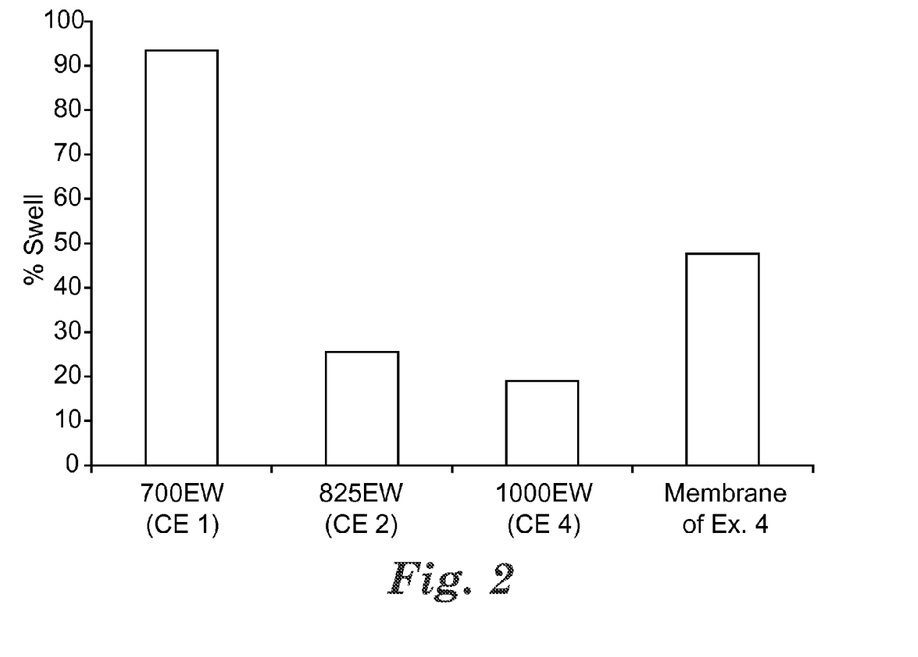
FIG. 2 is a graph of swelling behavior of the proton exchange membrane described in Example 4, as measured in the Swell/Water Uptake Test.
Figure 3:
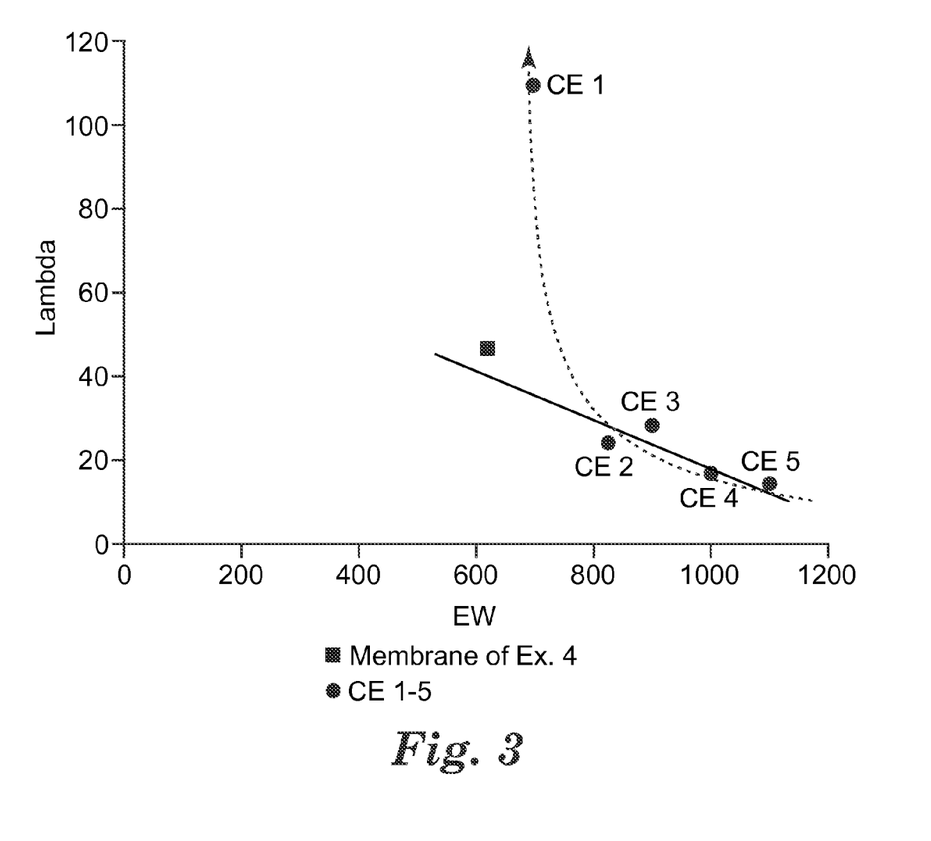
FIG. 3 is a graph of hydration performance for the proton exchange membrane described in Example 4, as a plot of EW (equivalent weight) versus "lambda" (number of equivalents (moles) of water absorbed by a membrane per equivalent of sulfonic acid groups present in the membrane), as measured in the Swell/Water Uptake Test.

Data shown in FIG. 1 includes conductivity values as a function of % relative humidity for duplicate lots of both an 825 EW Control material and PEM samples prepared according to Example 4. Data shown in FIG. 2 includes % swell values for the PEM prepared according to Example 4 as well as the indicated comparative example samples. Data shown in FIG. 3 includes a plot of the number of water molecules per sulfonic acid group as a function of EW for the PEM prepared according to Example 4 in comparison with comparative examples CE 1 to CE 5.

Various modifications and alterations of this disclosure will become apparent to those skilled in the art without departing from the scope and principles of this disclosure, and it should be understood that this disclosure is not to be unduly limited to the illustrative embodiments set forth hereinabove.

We claim:

1. A polymer electrolyte composition comprising a polymer having pendent groups according to formula V:

—(—SO$_2$—NZ—SO$_2$—R$_f$—)$_m$—(SO$_3$Y)$_p$  (V)

wherein the polymer is highly fluorinated;
where m is 1-6; p is at least 1; and Y is chosen from the group consisting of a monovalent cation, and a polyvalent cation;
wherein R$_f$ is a multivalent fluorochemical group selected from the group consisting of (i) a highly fluorinated alkylene, (ii) a perfluoroalkylene, and (iii) a perfluoroether; which are branched, unbranched, or cyclic; and
wherein Z is chosen from the group consisting of a monovalent cation, and a polyvalent cation, wherein the composition is a suspension or a solution.

2. The polymer electrolyte composition of claim 1 wherein the polymer is perfluorinated.

3. The polymer electrolyte composition of claim 1 wherein the R$_f$ group is a (—CF$_2$—)$_n$ group, wherein n is 3 and m is 1.

4. The polymer electrolyte composition to claim 1 wherein said pendent groups are according to formula VI:

—R$^3$—SO$_2$—NZ—SO$_2$(CF$_2$)$_n$SO$_3$Y  (VI)

where n is 1-6; Y is chosen from the group consisting of a monovalent cation, and a polyvalent cation; and R$^3$ is a branched or unbranched highly fluorinated aliphatic group comprising 1-15 carbon atoms and 0-4 oxygen atoms; and
wherein Z is chosen from the group consisting of a monovalent cation, and a polyvalent cation.

5. The polymer electrolyte composition of claim 1 further comprising a polar solvent.

6. The polymer electrolyte composition of claim 1 further comprising a stabilizing additive.

7. The polymer electrolyte composition of claim 6 wherein the stabilizing additive comprises an element selected from the group consisting of Mn and Ce.

8. The polymer electrolyte composition of claim 1 wherein R$_f$ is a multivalent fluorochemical group perfluoroalkylene.

9. A composite membrane comprising a porous support matrix, wherein the pores are substantially impregnated with the polymer electrolyte composition according to claim 1.

10. A method of making a polymer according to claim 1 comprising the step of reacting a polymer having pendent groups according to formula VII:

—CF$_2$—SO$_2$—NH$_2$  (VII)

with a compound according to formula II:

FSO$_2$(CF$_2$)$_n$SO$_2$F  (II)

where n is 1-6.

11. A method of making a polymer according to claim 1 comprising the step of reacting a polymer having pendent groups according to formula VIII:

—CF$_2$—SO$_2$F  (VIII)

with a compound according to formula IX:

HSO$_3$(CF$_2$)$_n$—SO$_2$—NH$_2$  (IX)

where n is 1-6.

12. A polymer electrolyte comprising a polymer cast from the polymer electrolyte composition according to claim 1.

13. An electrode comprising the polymer electrolyte according to claim 12.

14. A polymer electrolyte membrane comprising the polymer electrolyte according to claim 12.

15. A membrane electrode assembly comprising the polymer electrolyte membrane according to claim 13.

16. The polymer electrolyte composition of claim 1, wherein Z is selected from the group consisting of H+, cations of alkali metals, cations of alkaline earth metals, and alkylammonium cations.

17. The polymer electrolyte composition of claim 4, wherein Z is selected from the group consisting of H+, cations of alkali metals, cations of alkaline earth metals, and alkylammonium cations.

* * * * *